(12) United States Patent
Akizumi et al.

(10) Patent No.: US 8,946,318 B2
(45) Date of Patent: Feb. 3, 2015

(54) KIT OF MATERIAL FOR REPAIRING DENTIN

(71) Applicant: Tokuyama Dental Corporation, Tokyo (JP)

(72) Inventors: Hironobu Akizumi, Tokyo (JP); Chika Toriyabe, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 0 days.

(21) Appl. No.: 14/027,936

(22) Filed: Sep. 16, 2013

(65) Prior Publication Data

US 2014/0017638 A1      Jan. 16, 2014

Related U.S. Application Data

(63) Continuation-in-part of application No. PCT/JP2012/056646, filed on Mar. 15, 2012.

(30) Foreign Application Priority Data

Mar. 18, 2011   (JP) ................... 2011-060539

(51) Int. Cl.
*A61C 5/04*    (2006.01)
*A61K 6/00*    (2006.01)

(52) U.S. Cl.
CPC ............... *A61C 5/04* (2013.01); *A61K 6/0002* (2013.01); *A61K 6/0005* (2013.01); *A61K 6/0023* (2013.01); *A61K 6/0058* (2013.01)
USPC ........................ 523/115; 433/228.1

(58) Field of Classification Search
None
See application file for complete search history.

(56) References Cited

U.S. PATENT DOCUMENTS

| 2001/0049082 | A1 | 12/2001 | Kerschbaumer et al. | |
| 2010/0081728 | A1* | 4/2010 | Uchida et al. | 523/105 |
| 2011/0172323 | A1* | 7/2011 | Akizumi et al. | 522/25 |
| 2011/0236857 | A1 | 9/2011 | Rheinberger et al. | |
| 2013/0005846 | A1* | 1/2013 | Yamazaki et al. | 521/149 |
| 2013/0032241 | A1* | 2/2013 | Yamaguchi et al. | 141/2 |
| 2013/0096226 | A1* | 4/2013 | Toriyabe et al. | 523/115 |
| 2013/0324635 | A1* | 12/2013 | Shimizu et al. | 522/173 |

FOREIGN PATENT DOCUMENTS

| JP | 03-178650 A | 8/1991 |
| JP | 1997-169613 A | 6/1997 |

(Continued)

OTHER PUBLICATIONS

International Search Report dated Apr. 5, 2012, mailed Apr. 17, 2013.

(Continued)

*Primary Examiner* — James J Seidleck
*Assistant Examiner* — Peter A Salamon
(74) *Attorney, Agent, or Firm* — Norris McLaughlin & Marcus, P.A.

(57) ABSTRACT

The present invention discloses a kit of material for dentin restoration including a combination of a plurality of kinds of curable pastes each having a different hue, wherein each of the curable pastes exhibits L* of 55 to 75 and a fluctuation range of L* of 3 or less in a CIELab color system when the color of a cured body with a thickness of 3.0 mm obtained by curing the pastes is measured against a black background, and a method for producing the kit of material for dentin restoration.

7 Claims, 2 Drawing Sheets

(56) References Cited

FOREIGN PATENT DOCUMENTS

| JP | 2008-068079 A | 3/2008 |
|---|---|---|
| JP | 2009-022433 A1 | 2/2009 |
| JP | 2010-083833 A | 4/2010 |

OTHER PUBLICATIONS

English Translation of International Search Report dated Apr. 5, 2012, mailed Apr. 17, 2013.

* cited by examiner

Fig. 1

Fig. 2

US 8,946,318 B2

KIT OF MATERIAL FOR REPAIRING DENTIN

This application is a Continuation-in-part of PCT/JP2012/056646 filed Mar. 15, 2012, which claims foreign priority benefit under 35 U.S.C. §119 of Japanese application Nos. 2011-060539 filed Mar. 18, 2011.

TECHNICAL FIELD

The present invention relates to a kit of materials for dentin restoration. This kit comprises a plurality of kinds of curable pastes which, when cured, exhibit substantially the same Value. More particularly, the present invention relates to the kit of materials for dentin restoration, which can beautifully restore damaged teeth by filling, in the form of layers, curable pastes in the damaged portion of the teeth and then curing the pastes.

BACKGROUND ART

In restoring a tooth damaged by dental caries, fracture, etc., a restorative material called "resin composite", which is a curable paste, is in wide use for its easy operation. This curable paste is ordinarily photo-curable. In recent years, the curable paste has been highly improved in mechanical strength and bond strength to tooth and, therefore, is in use not only for restoration of anterior teeth but also for posterior teeth which receive a high occlusal pressure.

Restoration of a tooth using a restorative material therefore is conducted generally in a manner mentioned in the following 1) to 3).

1) The damaged portion of a tooth damaged by dental caries or the like (the tooth is hereinafter referred to also as "to-be-restored tooth") is cut and removed, whereby a cavity is formed in the tooth.

2) On the inner surface of the cavity of the tooth, there is ordinarily coated an adhesive called "bonding agent". Then, air-blowing is conducted as necessary. Thereafter, the adhesive is irradiated with a light, whereby the inner surface of the cavity of the tooth is covered with the adhesive. Next, a curable paste is heaped up on the surface of the adhesive covering the above inner surface. The curable paste is photo-cured, whereby the cavity is filled.

3) As a final step, the cured body of the curable paste (referred to also as composite filling and restorative material) filled in the cavity is subjected to shape modification and polishing.

In tooth restoration, the restorative material used need be easily handled; the cured body of the composite filling and restorative material filled in the cavity needs to have high mechanical strength, etc.; and the tooth after restoration needs to be beautiful.

Natural tooth comprises dentin and enamel. Natural tooth differs in color tone (Hue, Chroma and Value) depending upon the portions. For example, the incisal region of natural tooth contains a thin dentin layer and is constituted substantially by enamel and, therefore, has high transparency. In contrast, the cervical region of tooth contains a thick dentin layer; therefore, is opaque and, as compared with the incisal resion, has high Value (degree of lightness or darkness) and high Chroma (intensity of the shade).

That is, in natural tooth, the Chroma and Value become lower from the cervical region of tooth containing a thick dentin layer toward the incisal resion of tooth containing a thin dentin layer. Thus, the color tone of tooth differs depending upon the portions of tooth. Accordingly, in tooth restoration, it is necessary to select the color tone of the restorative material used, in such a way that this color tone fits the to-be-restored portion of tooth, in order to allow the restored tooth to have high esthetics. For allowing the restored tooth to have esthetics, it is conducted that a plurality of kinds of curable pastes each differing in color tone are prepared, there is selected, from these curable pastes, a curable paste having a color tone closest to the color tones of to-be-restored tooth and teeth adjacent thereto (these adjacent teeth are referred to also as "the periphery of to-be-restored tooth"), and this selected curable paste is used for tooth restoration (Non-patent Literature 1).

The selection of the color tone of the curable paste actually used is conducted specifically as follows. Firstly, there is prepared a shade guide (a color sample) which is a collection of samples of cured bodies of curable pastes. Then, a dentist conducting tooth restoration compares the color tones of the cured body samples of the shade guide with the color tone of the periphery of to-be-restored tooth which is confirmed by looking into the mouth. Lastly, the dentist selects, based on the comparison, a curable paste corresponding to the cured body sample considered to have the color tone closest to that of the periphery of to-be-restored tooth.

When the damage of to-be-restored tooth is large and the cavity is deep, it is difficult to achieve the above color tone adjustment only by filling of a single kind of curable paste. When a tooth has a deep cavity (for example, class IV cavity), the color tone of the tooth cannot be determined by the color tone of tooth surface (enamel portion) alone. Actually, the color tone of tooth is observed in such a state that the color tones of tooth surface portion to inner portion (dentin portion) which can be seen through from the surface portion are blended and show gradation.

In order to reproduce this gradation of color tones, there is known a method in which curable pastes are filled each in the form of layer in the restoration of cavity. In this method, a curable paste of selected color tone is filled so as to occupy a given depth of cavity and then cured; this operation is repeated each time with a curable paste of different color tone; in this way, the delicate gradation of color tones is reproduced.

Ordinarily, a plurality of kinds of curable pastes for dentin restoration, for reproduction of the color tones of dentin are filled each in the form of layer in order from the innermost portion of cavity toward the surface portion of tooth; then, a curable paste for enamel restoration is filled in the form of layer on the last surface portion (for example, Non-patent Literature 1 and Non-patent Literature 2). Incidentally, in the above filling, it is common to cure the filled curable paste after filling of each curable paste.

PRIOR TECHNICAL LITERATURES

Non-Patent Literatures

Non-patent Literature 1: "Adhesion Yearbook 2006", first edition, edited by Hideo Matsumura and Junji Tagami, published from QUINTESSENCE Publishing Co., Ltd. on August, 2006, p. 129 to 137

Non-patent Literature 2: "Science and Technique of restoration with Resin Composite", first edition, written by Masashi Miyazaki, published from QUINTESSENCE Publishing Co., Ltd. on January, 2010, P. 48 to 49

DISCLOSURE OF THE INVENTION

Task to be Achieved by the Invention

In the restoration of deep cavity by the above-mentioned method of filling curable pastes each in the form of layer, the Hue and Chroma (these two are called, in combination, "chromaticity") after restoration can be allowed to be well conformed to those of the periphery of to-be-restored tooth. However, the Value after restoration is difficult to confirm to that of the periphery and there appears often a phenomenon that the restored portion looks bright or dark as compared to the periphery of to-be-restored tooth.

This phenomenon occurs due to the man's sensitivity to color. When man senses a color, importance is placed particularly on chromaticity (Hue and Chroma) among the three elements of color tone, i.e. Hue, Chroma and Value. As a result, in selecting a curable paste by referring to the shade guide, it is preferentially conducted unconsciously to confirm the chromaticity of the cured body of curable paste to that of the periphery of to-be-restored tooth.

Curable pastes of different chromaticities are prepared so that they can meet to various chromaticities of the tooth to-be-restored. However, no curable pastes are available currently which have a large number of different Values in addition to Hues. The reason is that a massive number of curable pastes need be prepared. That is, there is ordinarily no such case that each curable paste having a given chromaticity is prepared in a plurality of kinds each having a different Value.

As described above, when a curable paste is selected based on the chromaticity determined by the man's sensitivity to color, the Value of the curable paste is determined automatically by the chromaticity of the curable paste selected. As described above, in filling, in the form of layers, curable pastes in a to-be-restored tooth, a plurality of curable pastes of different chromaticities are filled in the form of layers correspondently to the depth of the cavity. Accordingly, with the filling in the form of layers, the Value of each portion of the tooth after restoration shows large fluctuation depending upon the portions, independently of the actual Value of the tooth to be restored.

In order to avoid this problem, the adjustment of Value in the filling of curable pastes in the form of layers is conducted, in actual treatment, by controlling the thickness of each layer. That is, in filling any one curable paste in the form of layer, the brightness of the layer formed is higher as the layer is thicker and is lower as the layer is thinner; therefore, the thickness of each layer is determined depending upon the Value of the curable paste selected and the overall Value of restored portions is allowed to confirm to the overall Value of the to-be-restored tooth.

However, the curable pastes used for filling in the form of layers fluctuate largely in Value. Therefore, it is not easy to design the thickness of each curable paste to be filled in the form of layer, before filling, in such a manner that the overall Value of restored portions conforms to that of the to-be-restored tooth.

A dentist fills each curable paste in the form of layer with changing the thickness of each layer on the basis of his experience while anticipating the overall Value of restored portions. However, such anticipation is difficult for a dentist of little experience, hampering smooth treatment. The dentin (which is inside tooth), in particular, has high Value, is thick, and changes largely in Value depending upon the portions of dentin; therefore, a plurality of layers need be laminated for the dentin portions alone. However, it is very difficult as mentioned above to design the thickness of each laminated layer so that the overall Value of these laminated layers conform to the Value of the periphery of to-be-restored tooth. As a result, in restoration of dentin, it often occurs that the overall Value of restored dentin portions differs largely from the Value of the periphery thereof. In such a case, the improvement of this difference is impossible by filling of a nearly transparent curable paste for restoration of enamel as a surface layer.

Thus, as described above, there occur failure cases that, after treatment, the Value of the restored portions of tooth does not sufficiently conform to the Value of the periphery thereof.

For the above reasons, it is a big task in restoration of cavity, by filling a plurality of kinds of curable pastes into the cavity in the form of layers, to easily conform not only the chromaticity of the restored tooth portions but also the Value thereof, to those of to-be-restored tooth.

Means for Achieving the Task

The present inventors made a study in order to achieve the above task. As a result, it was found that the above task could be achieved by allowing the curable pastes of different color tones constituting a kit of materials for dentin restoration to have the same Value. The finding has led to the completion of the present invention.

The present invention is described below.

[1] A kit of materials for dentin restoration, comprising a combination of a plurality of kinds of curable pastes each having a different color tone, wherein each curable paste exhibits a Value $L^*$ of 55 to 75 and a fluctuation range of the Value $L^*$, of 3 or less in the CIELab color system when the cured body of 3.0 mm in thickness obtained by curing the curable paste is measured for color against a black background.

[2] The kit of materials for dentin restoration according to [1], wherein each curable paste, when the cured body of 3.0 mm in thickness obtained by curing the curable paste is measured for color against a black background, exhibits $a^*$ of −5.0 to 3.0 and $b^*$ of 0 to 20 in the CIELab color system, at least either of $a^*$ and $b^*$ of the cured bodies differ from each other by 0.3 or more in the case of $a^*$ and by 1.0 or more in the case of $b^*$, and each cured body has a different chromaticity.

[3] The kit of materials for dentin restoration according to [1], wherein each curable paste exhibits a contrast ratio of 0.55 to 0.75 when the cured body of 1.0 mm in thickness obtained by curing the curable paste is measured for the contrast ratio against a black background.

[4] A kit of materials for tooth restoration, comprising
the kit of materials for dentin restoration according to any one of [1] to [3], and
a kit of materials for enamel restoration, comprising of a plurality of kinds of curable pastes each having a different color tone when the cured body obtained by curing the curable paste is measured for color against a black background.

[5] The kit of materials for tooth restoration according to [4], wherein each of the curable pastes constituting the kit of materials for enamel restoration exhibits Value $L^*$ of 45 to 65, $a^*$ of −5.0 to 3.0 and $b^*$ of −5 to 20, in the CIELab color system, when the cured body of 3.0 mm in thickness obtained by curing each curable paste is measured for color against a black background.

[6] The kit of materials for tooth restoration according to [4], wherein each of the curable pastes constituting the kit of materials for enamel restoration exhibits a contrast ratio of 0.20 to 0.55 when the cured body of 1.0 mm in thickness obtained by curing each curable paste is measured for the contrast ratio.

[7] A method for producing a kit of materials for dentin restoration set forth in [1], wherein the Value $L^*$ of each of a plurality of kinds of curable pastes is adjusted by changing the addition amount of a white coloring agent, while retaining the chromaticity a* and b* of each curable paste.

Effect of the Invention

When the dentin of tooth is restored by conducting filling, in the form of layers, using the kit of materials for dentin restoration, of the present invention, the restoration can be conducted with simple operation and not only chromaticity but also Value of the restored tooth portions can be well conformed to those of the periphery thereof. Therefore, restoration of tooth can be conducted beautifully with easy operation when the kit of present invention is used in combination with the kit of materials for enamel restoration.

EXPLANATION OF NUMERICAL SYMBOLS

1 is an artificial teeth.
2 is an upper right central incisor.
3 is a class IV cavity.
4 is a restored portion.
D is the depth of cavity.
H is the height of cavity.
W is the width of cavity.

MODE FOR CARRYING OUT THE INVENTION

First, explanation is made on the properties related to color tone, used in the present invention.
<L* (Value)>
This is a measure indicating brightness and is measured according to JIS Z 8729. A standard light C is applied to a sample plate of 3.0 mm in thickness in the thickness direction against a black background. The reflected light is measured and L* value in the CIELab color system is read. A L* value closer to 100 indicates that the sample plate is brighter, and L* value closer to 0 indicates that the sample plate is darker.
<a*, b*(Chromaticity)>
This is an index indicating Hue and Chroma and is measured according to JIS Z 8729. A standard illuminant C is applied to a sample plate of 3.0 mm in thickness in the thickness direction against a black background. The reflected light is measured and a* value and b* value in the CIELab color system are read. The a* and b* indicate each a direction of color. The a* indicates a red direction; −a* indicates a green direction; b indicates a yellow direction; and −b* indicates a blue direction. In each of them, a larger Value indicates a more vivid color and a smaller Value indicates a duller color.
<Contrast Ratio>
This is a measure indicating transparence and is calculated using the Y value (of brightness) of the tristimulus values of XYZ color system specified by JIS Z 8701. A black background or a white background is contacted with the back side of a sample plate of 1.0 mm in thickness. A standard illuminant C is applied to the sample plate from its surface in the thickness direction. The reflected light is measured and a Y value is read. The Y value when the black background is used, is taken as Yb; and the Y value when the white background is used, is taken as Yw. The contrast ratio (C) of the sample plate is determined by Yb/Yw. A C value closer to 1 indicates an opaque material, and a C value closer to 0 indicates a transparent material.

The kit of materials for dentin restoration, of the present invention is constituted by a plurality of curable pastes, and the cured body of each curable paste has a different color tone. The curable pastes constituting the present kit are such that the cured bodies obtained by curing the curable pastes are different from each other in at least either of their Hues and Chroma. That is, the present kit is constituted by a plurality of curable pastes whose cured bodies have each a different chromaticity.

The number of the curable pastes constituting the present kit is ordinarily 2 to 20, preferably 3 to 18. By constituting the present kit with the curable pastes of such a number, the present kit can provide a Hue and a chroma, which conform well to the dentin of the man's tooth to be restored and which also conform sufficiently to the fluctuation of Hue and chroma among dentin portions or among individuals.

With respect to the Hue and Chroma of the cured body of each curable paste, a required Hue and a required Chroma are selected appropriately by referring to the A shade (reddish brown), B shade (reddish yellow), C shade (gray) and D shade (reddish gray) provided in an ordinary shade guide ("VITA-PAN Classical" is most common).

The a* is selected in a range of −5.0 to 3.0, preferably −4.0 to 2.0 so that the Hue of cured body can well conform to that of dentin. The b* is selected in a range of 0 to 20, preferably 1 to 19.

As mentioned above, the present kit is constituted by a plurality of curable pastes which, when cured, show such color tones that at least either of a* and b* are different from each other. The difference of color tones between cured bodies is preferably 0.3 or more, more preferably 0.5 or more, particularly preferably 0.7 or more in the case of a* and, in the case of b*, preferably 1.0 or more, more preferably 1.5 or more, particularly preferably 2.0 or more.

When there are prepared color tones of A shade (reddish brown), B shade (reddish yellow), C shade (gray) and D shade (reddish gray) according to the shade guide "VITAPAN Classical", the difference of color tones between curable pastes of same type having close color tones is preferably 3.0 or less, particularly preferably 2.0 or less in the case of a* and, in the case of b*, preferably 7.0 or less, particularly preferably 5.0 or less.

The principal characteristic of this invention is that each of the cured bodies obtained by curing the above-mentioned plurality of curable pastes of different color tones shows a L* (Value) fluctuating in a given range of 55 to 75, preferably 57 to 70, that is, substantially the same L* (Value). Thereby, even when curable pastes different in a* and/or b* are filled in the form of layers, the cured bodies thereof show the same L* always. As a result, the thickness of curable pastes filled in the form of layers in dentin portion can be predicted easily by considering the range of Value adjustment by selection of curable pastes for restoration of enamel (tooth surface). Thus, the overall Value of to-be-restored portion can be well conformed to the Value of the periphery of to-be-restored tooth.

As mentioned previously, in conventional kits of materials for dentin restoration, the color tone of each curable paste is determined by putting emphasis on hue and Chroma and no strict control is made on Value. That is, Value is controlled in such an extent that there is no deviation from the above-mentioned L* range (55 to 75). Accordingly, in conventional kits of materials for dentin restoration, the Value of the cured body of each curable paste ordinarily fluctuates randomly to the change of the Hue and Chroma of the cured body (roughly speaking, the Value tends to decrease as the Chroma increases). The Value is not set substantially at the same value, unlike in the present invention.

A cured body of each curable paste, having a L* (Value) of higher than 75 is too high in Value. In this case, it is difficult to allow the Value of restored portion to well conform to the Value of the periphery of to-be-restored tooth by controlling the filling thickness of each curable paste. That is, the restored portion looks very white as compared to the periphery thereof.

In contrast, a cured body of each curable paste, having a L* (Value) of lower than 55 is too low in Value. Also in this case, it is difficult to allow the Value of restored portion to well conform to the Value of the periphery of to-be-restored tooth by controlling the filling thickness of each curable paste. That is, the restored portion looks dark.

In the present invention, that cured bodies of curable pastes have substantially the same Value, indicates a case in which their Values agree completely to each other in all figures including the first digit figure. There is also included a case in which, when the Values of cured bodies are controlled by a dentist by changing the filling thickness of each curable paste, the Values differ from each other only slightly in such an extent that the cured bodies are recognized to have the same Value. Specifically speaking, cured bodies of curable pastes are defined to have substantially the same Value when the L* of the cured bodies fluctuate in a range (the difference of the maximum Value L* and the minimum Value L*) of 3 or less, preferably 2 or less.

In the kit of materials for dentin restoration, of the present invention, the cured body of each curable paste has a contrast ratio of preferably 0.55 to 0.75. When the contrast ratio is in this range, the cured body of each curable paste has a transparency well conforming to the transparency of dentin.

Each of the present curable pastes having the above-mentioned color tones is generally made of a polymerizable composition containing a polymerizable monomer, a polymerization initiator, a filler and coloring agents.

<Polymerizable Monomer>

The polymerizable monomer compounded in each curable paste of the present invention may be any polymerizable monomer used in a composite resin in the dental field. Preferred is a polymerizable monomer of acrylate type or methacrylate type (hereinafter, the two types are referred to as (meth)acrylate type, in some cases). A monomer of polyfunctional (meth)acrylate type is more preferred from the standpoints of curing rate of monomer, and mechanical properties, water resistance, coloring resistance, etc. of cured body.

As examples of the preferably usable polymerizable monomer of polyfunctional (meth)acrylate type, there can be mentioned those shown in the following (I) to (III).

(I) Bifunctional Polymerizable Monomer
i) Aromatic Compound Type 2,2-Bis(methacryloyloxyphenyl)propane, 2,2-bis[4-(3-methacryloyloxy)-2-hydroxypropoxyphehyl]propane (hereinafter abbreviated as bis-GMA), 2,2-bis(4-methacryloyloxyphenyl)propane, 2,2-bis(4-methacryloyloxypolyethoxyphenyl)propane (hereinafter abbreviated as D-2.6E), 2,2-bis(4-methacryloyloxydiethoxyphenyl) propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacyloyloxydiethoxyphenyl)-2(4-methacryloyloxytriethoxyphenyl)propane, 2(4-methacryloyloxydipropoxyphenyl)-2-(4-methacryloyloxytriethoxyphenyl)propane, 2,2-bis((4-methacryloyloxypropoxyphenyl)propane, 2,2-bis(4-methacryloyloxyisopropoxyphenyl)propane; and acrylates corresponding to these methacrylates Diadducts obtained by an addition reaction between an OH group-containing vinyl monomer (e.g. a methacrylate such as 2-hydroxyethyl methacrylate, 2-hydroxypropyl methacrylate or 3-chloro-2-hydroxypropyl methacrylate, or an acrylate corresponding to such a methacrylate) and an aromatic group-containing diisocyanate compound (e.g. diisocyanato methylbenzene or 4,4'-diphenylmethane diisocyanate); etc.

ii) Aliphatic Compound Type

Ethylene glycol dimethacrylate, diethylene glycol dimethacrylate, triethylene glycol dimethacrylate (hereinafter abbreviated as 3G), tetraethylene glycol dimethacrylate, neopentylglycol dimethacrylate, 1,3-butanediol dimethacrylate, 1,4-butanediol dimethacrylate, 1,6-hexanediol dimethacrylate; and acrylates corresponding to these methacrylates Diadducts obtained by addition of an OH group-containing vinyl monomer (e.g. a methacrylate such as 2-hydroxyethyl methacrylate, 2-hydroxypropyl methacrylate or 3-chloro-2-hydroxypropyl methacrylate, or an acrylate corresponding to such a methacrylate) and a diisocyanate compound (e.g. hexamethylene diisocyanate, trimethylhexamethylene diisocyanate, diisocyanato methylcyclohexane, isophorone diisocyanate, or methylene-bis(4-cyclohexyl isocyanate))

1,2-Bis(3-methacryloyloxy-2-hydroxypropoxy)ethyl, etc.

(II) Trifunctional Polymerizable Monomer

Methacrylates such as trimethylolpropane trimethacrylate, triethylolethane trimethacrylate, pentaerythritol trimethacrylate, trimethylolmethane trimethacrylate and the like; acrylates corresponding to these methacrylates; etc.

(III) Tetrafunctional Polymerizable Monomer

Diadducts obtained by addition of pentaerythritol tetramethacrylate, pentaerythritol tetra-acrylate, or a diisocyanate compound (e.g. diisocyanato methylbenzene, diisocyanato methylcyclohexane, isophorone diisocyanate, hexamethylene diisocyanate, trimethyl hexamethylene diisocyanate, methylene-bis(4-cyclohexyl isocyanate), 4,4-diphenylmethane diisocyanate, or tolylene-2,4-diisocyanate) and glycidol dimethacrylate; etc.

These polyfunctional methacrylate type polymerizable monomers may be used as necessary in combination of a plurality of kinds.

There may be further used as necessary a monofunctional (meth)acrylate type monomer such as methacrylate (e.g. methyl methacrylate, ethyl methacrylate, isopropyl methacrylate, hydroxyethyl methacrylate, tetrahydrofurfuryl methacrylate, or glycidyl methacrylate) or acrylate corresponding to such a methacrylate, and a polymerizable monomer other than the above (meth)acrylate type monomer.

<Polymerization Initiator>

Any known polymerization initiator may be used as long as it can polymerize and cure the above-mentioned polymerizable monomers. A photopolymerization initiator is used ordinarily, in many cases; however, a chemical polymerization initiator (normal temperature redox initiator), a thermal polymerization initiator or the like is usable as well. The polymerization initiator may be used in one kind or in combination of two or more kinds.

As the photopolymerization initiator, there may be used benzoin alkyl ethers such as benzoin methyl ether, benzoin ethyl, ether, benzoin isopropyl ether and the like; benzyl ketals such as benzyl dimethyl ketal, benzyl diethyl ketal and the like; diaryl ketones such as benzophenone, anthraquinone, thioxanthone and the like; α-diketones such as diacetyl, benzyl, camphorquinone, 9,10-phenanthraquinone and the like; bisacylphosphine oxides such as bis-(2,6-dichlorobenzoyl)phenylphosphine oxide, bis-(2,6-dichlorobenzoyl)-2,5-dimethylphenylphosphine oxide, bis-(2,6-dichloro-benzoyl)-4-propylphenylphosphine oxide, bis-(2,6-dichlorobenzoyl)-1-naphthylphosphine oxide, bis(2,4,6-trimethylbenzoyl)-phenylphosphine oxide and the like; and etc.

The above photopolymerization initiator is used preferably in combination with a reducing compound. As the reducing compound, there can be mentioned, for example, tertiary amines such as 2-(dimethylamino)ethyl methacrylate, ethyl 4-dimethylaminobenzoate, N-methyldiethanolamine, dimethylaminobenzaldehyde, terephthalaldehyde and the like; sulfur-containing compounds such as 2-mercaptobenzoxazole, 1-decanthiol, thiosalicylic acid, thiobenzoic acid and the like; and N-phenylalanine.

It is also preferred embodiment to add a photo-induced acid-generating agent in order to enhance the activity of the photopolymerization initiator. As the photo-induced acid-generating agent, there can be mentioned, for example, a diaryl iodonium salt type compound, a sulfonium salt type compound, a sulfonic acid ester compound, a halomethyl-substituted S-triazine derivative, and a pyridinium salt type compound. When the photo-induced acid-generating agent is used, the photopolymerization initiator is preferably an α-diketone (e.g. camphorquinone) and it is more preferred to use, in combination, a reducing compound (e.g. 4-dimethylaminobenzoic acid).

As the thermal polymerization initiator, there can be mentioned peroxides such as benzoyl peroxide, p-chlorobenzoyl peroxide, tert-butyl peroxy-2-ethylhexanoate, tert-butyl peroxydicarbonate, diisopropyl peroxydicarbonate and the like; and azo compounds such as azobisisobutyronitrile and the like.

As the chemical polymerization initiator, there can be mentioned, for example, a combination of the above-mentioned peroxide used as a thermal polymerization initiator and the tertiary amine shown as an example of the reducing compounds preferably used in combination with the photopolymerization initiator.

In each curable paste, the amount of the polymerization initiator used is preferably 0.01 to 5 mass parts, more preferably 0.1 to 5 mass parts relative to 100 mass parts of the polymerizable monomer. The polymerization initiator is used in this range in such an amount that the desired color tone of cured body is not affected.

<Filler>

As the filler, there may be used any material which is usable as a filler for composite resin in the dental field. Specifically, there can be mentioned inorganic powders such as amorphous silica, silica-zirconia, silica-titania, quartz, alumina, barium glass, zirconia, titania, lanthanoide, colloidal silica and the like. These inorganic powders may be surface-treated with a silane coupling agent or the like. There may be also used an organic powder or an organic-inorganic composite powder. A filler used particularly preferably in the present invention is spherical composite oxide particles which are produced by the methods described in JP-A-1983-110414, JP-A-1983-156524, etc.

In each curable paste, the amount of the filler used is preferably 200 to 1,900 mass parts, more preferably 300 to 900 mass parts relative to 100 mass parts of the polymerizable monomer. The filler is used in this range in such an amount that the desired color tone of curable paste is not affected.

<Coloring Agents>

The polymerizable composition containing the above-mentioned polymerizable monomer, polymerization initiator and filler is allowed to have a desired color tone by compounding therein coloring agents. The coloring agents used include pigments or dyes.

As the pigments, there can be mentioned white pigments such as titanium oxide, zinc oxide, zirconium oxide and the like; red pigments such as red iron oxide, molybdenum red, chromophthal red and the like; yellow pigments such as yellow iron oxide, titanium yellow, chrominum oxide, chromophthal yellow; blue pigments such as cobalt blue, ultramarine, prussian blue, chromophthal blue, phthalocyanine blue and the like; and black pigments such as black iron oxide, carbon black and the like.

As the dyes, there can be mentioned, for example, red dyes of KAYASET RED g (Nippon Kayaku Co., Ltd.) and KAYASET RED B (Nippon Kayaku Co., Ltd.); yellow dyes such as KAYASET Yellow 2G, KAYASET Yellow GN and the like; and dyes such as KAYASET Blue N, KAYASET Blue G, KAYASET Blue B and the like.

<Adjustment of Color Tone>

A plurality of above-mentioned coloring agents are combined and their amounts are adjusted, whereby each curable paste, when cured, can exhibit a a* of −5.0 to 3.0 and a b* of 0 to 20. Incidentally, such values of a* and b* are for conforming the cured body of curable paste to the periphery of to-be-restored tooth.

However, when coloring is made based only on the above Hue and Chroma, Value L* fluctuates largely as well. Accordingly, each curable paste does not exhibit substantially the same L*. In general, as coloring agents are compounded in a larger amount to enhance Chroma, Value drops.

In the present invention, Value L* is allowed to be substantially at the same level selected in a range of 55 to 75 while Hue and Chroma are varied each in the above-mentioned range. A method for achieving this is described below.

In the method, a plurality of coloring agents are combined to adjust the a* and b* of each cured body, and the amount of a white coloring agent is increased or decreased to adjust the Value L* of each cured body. Increase in the amount of white coloring agent can give a higher Value and decrease in the amount of white coloring agent can give a lower Value.

Specifically explaining, first, a* and b* are adjusted without paying much attention to L*. In this case, when the L* obtained is lower than the level intended in the present invention, the addition amounts of red, yellow, blue and black coloring agents (these have a large influence on chromaticity), are increased and further the addition amount of white coloring agent is increased. By such an operation, the value of L* is adjusted at an intended level while the values of a* and b* are being retained.

Meanwhile, when a* and b* are adjusted without paying much attention to L* and the L* obtained is higher than the level intended in the present invention, the addition amounts of red, yellow, blue and black coloring agents (these have a large influence on chromaticity), are decreased and further the addition amount of white coloring agent is decreased. By such an operation, the value of L* is adjusted at an intended level while the values of a* and b* are being retained.

In general, when pigments are used as the coloring agents, the addition amounts thereof are preferably 0.0005 to 0.5 mass part, more preferably 0.01 to 0.3 mass part relative to 100 mass parts of the polymerizable monomer used. The addition amount of white coloring agent used in the above-mentioned adjustment of L* is ordinarily preferred to be 0.0001 to 0.3 mass part and more preferred to be 0.0005 to 0.2 mass part.

<Kit of Materials for Enamel Restoration>

The kit of materials for dentin restoration, of the present invention can be used as it is. However, it may be combined with a known kit for enamel restoration to use as a kit of materials for tooth restoration.

Next, explanation is made on a kit of materials for enamel restoration which is preferably used to combine with the kit of materials for dentin restoration, of the present invention and obtain a kit of materials for tooth restoration.

The kit of materials for enamel restoration comprises a plurality (ordinarily 2 to 20 kinds) of curable pastes which, when cured, exhibit different color tones, similarly to the kit of materials for dentin restoration. The kit of materials for enamel restoration has higher transparency as compared with the kit of materials for tooth restoration. Each curable paste constituting the kit of materials for enamel restoration, (when made into a cured body of 1.0 mm in thickness), ordinarily shows a contrast ratio of preferably 0.20 to 0.55.

The cured body of 3.0 mm in thickness, of the curable paste preferably exhibits a Value L* of 45 to 65 in the CIELab color system when measured against a black background. Incidentally, the cured body of 3.0 mm in thickness preferably gives a* of −5.0 to 3.0 and b* of −5 to 20 in the CIELab color system when measured against a black background.

Each curable paste constituting the kit of materials for enamel restoration is generally made of a polymerizable composition containing components such as polymerizable monomer, polymerization initiator, filler, coloring agents and the like. These components are preferably the same as explained for each curable paste constituting the kit of materials for dentin restoration.

Adjustment of color tone of each curable paste is preferably made in the same manner as explained for each curable paste constituting the kit of materials for dentin restoration.

The kit of materials for tooth restoration, which is a combination of the kit of materials of dentin restoration, of the present invention and the kit of materials for enamel restoration may further contain, as constituent members, a composite filling and restorative material and an auxiliary member.

The composite filling and restorative material includes a composite filling and restorative material of desired contrast ratio and color tone, each different from those mentioned above. As an example of such a composite filling and restorative material, there is a white composite filling and restorative material of low chromaticity whose color tone is adjusted so as to conform to the tooth after whitening. There is also a composite filling and restorative material of high transparency which can provide an opalescent effect seen at the top end portion of natural tooth.

As examples of the auxiliary member, there can be mentioned those necessary for manufacture of filling and restorative material, such as opaque resin, brush, polisher and the like.

Hereinafter, the present invention is described specifically by way of Examples. However, the present invention is not restricted by these Examples. Incidentally, the abbreviations (given inside parentheses) of the compounds used in the following Examples and Comparative Examples are shown below.

(A) Radically Polymerizable Monomers
　　2,2-Bis[(3-methacryloyloxy-2-hydroxypropyloxy)phenyl]propane (bis-GMA)
　　Triethylene glycol dimethacrylate (3G)

(B) Photopolymerization Initiators
　　B1) α-diketone
　　　Camphorquinone (CQ)
　　B2) Aromatic amine compound
　　　Ethyl N,N-dimethyl p-benzoate (DMBE)
(C) Polymerization Inhibitor
　　Hydroquinone monomethyl ether (HQME)
(D) Fillers
　　Spherical silica-zirconia filler (D-1)
　　The average particle diameter of primary particles: 0.2 μm; surface-treated with γ-methacryloyloxypropyltrimethoxysilane
　　Organic-inorganic composite filler (D-2)
　　This organic-inorganic composite filler was prepared as follows.

15 mass parts of bis-GMA and 10 mass parts of 3G were mixed. In this mixture was dissolved 0.5 mass % of a polymerization initiator (azobisisobutyronitrile). Then, 75 mass parts of a filler (D-1) was added, followed by mixing, to obtain a paste.

The paste was heated at 95° C. for 1 hour in a nitrogen (0.5 MPa) atmosphere, to polymerize and cure the paste. The obtained cured body was ground using a vibration ball mill. To the ground cured body was added 0.02 mass % (relative to the ground cured body) of γ-methacryloyloxypropyltrimethoxysilane. The mixture was refluxed in ethanol at 90° C. for 5 hours to conduct a surface treatment. Thereby, an organic-inorganic composite filler of 30 μm in average particle diameter was obtained.

(E) Coloring Agents
　　E1) White pigment (titanium dioxide)
　　E2) Yellow pigment (Pigment Yellow)
　　E3) Red pigment (Pigment Red)
　　E4) Blue pigment (Pigment Blue)

The properties described in Examples and Comparative Examples were measured by the following methods.

(1) Measurement of Color Tone

Color tone was measured in accordance with JITS Z 8729. Specifically explaining, a curable paste was filled in a polyacetal-made mold of 3.00 mm in thickness, having a through-hole of 7 mm in diameter. A polypropylene film was placed on two surfaces of the mold. In this state, the curable paste was irradiated with a light for 30 seconds, using a light applicator for dental use (Tokuso Power Light, manufactured by TOKUYAMA DENTAL CORPORATION, light output density: 700 mW/cm$^2$). To the cured body obtained was applied a standard illuminant C. The color tone of the reflected light was measured against a black background, using a spectrophotometer (TC-1800 MKII, manufactured by TOKYO DENSHOKU Co., Ltd.), whereby the Value L* and chromaticity a* and b*, of the cured body, represented by the CIELab color system were obtained.

(2) Measurement of Contrast Ratio

A curable paste was filled in a polyacetal-made mold of 1.00 mm in thickness, having a through-hole of 7 mm in diameter. A polypropylene film was laminated on two surfaces of the mold. The curable paste was irradiated with a light for 30 seconds, using a light applicator for dental use (Tokuso Power Light, manufactured by TOKUYAMA DENTAL CORPORATION, light output density: 700 mW/cm$^2$). To the cured body obtained was applied a standard light C. The color tone of the reflected light was measured against a white background and also against a black background, using a spectrophotometer (TC-1800 MKII, manufactured by TOKYO DENSHOKU Co., Ltd.). A contrast ratio C was calculated from the respective Y values, using the following formula.

$$C(\text{contrast ratio}) = Yb(Y \text{ value against black background})/Yw(Y \text{ value against white background})$$

Example 1

Figure 1:
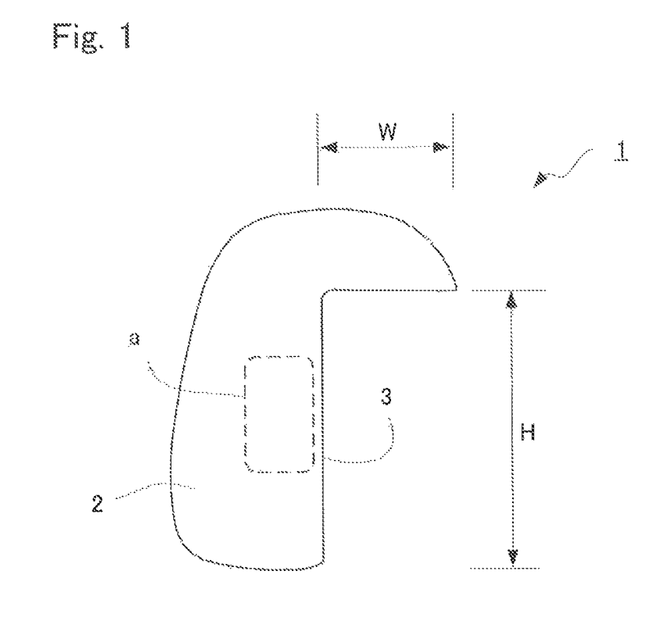
FIG. 1 is a front view of the model for tooth restoration, used in Examples and Comparative Examples.

In FIG. 1, 1 indicates a front view of a model for tooth restoration. The model 1 has a class IV cavity 3 of an upper right central incisor 2.

Figure 2:
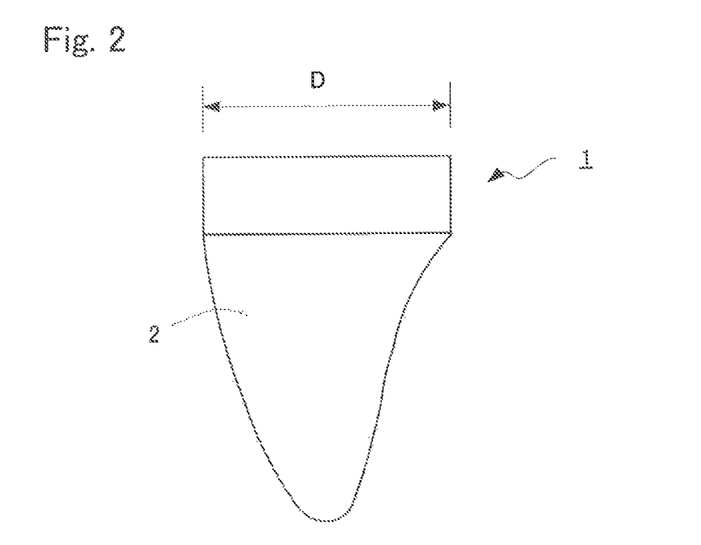
FIG. 2 is a right side view of the model for tooth restoration, of FIG. 1.

FIG. 2 is a right side view of the model 1. Tooth restoration was conducted using the model 1 for tooth restoration. In the model 1 for tooth restoration, the class IV cavity 3 has a depth D of 5 mm, a height H of 7 mm and a width W of 4 mm.

The artificial teeth was prepared in two kinds. One kind was a high-chromaticity model A in which the color tone of the portion a surrounded by a dotted line, in the periphery of the cavity had a delicately high Hue and a high Chroma in the range of the shade guide "A2 in VITAPAN Classical". The other kind was a low-chromaticity model B having a delicately low Hue and a low Chroma. These two models A and B has substantially the same Value.

Figure 3:
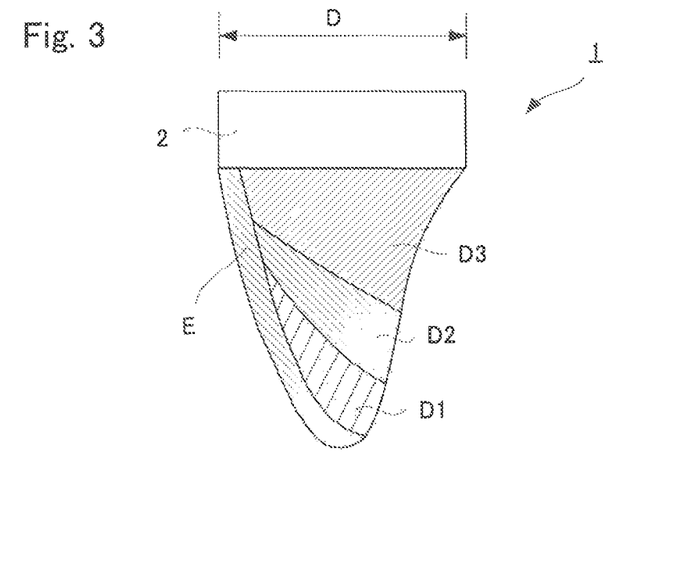
FIG. 3 is a sectional view indicating a state in which curable pastes of different color tones are filled in the form of layers in the class IV cavity formed in the model for tooth restoration, of FIG. 1.

It was judged to be appropriate that each class IV cavity 3 of the high-chromaticity model A and the low-chromaticity model B was restored by dividing the dentin portion in portions D1 to D3 as shown in the sectional view of FIG. 3. In the restoration, it was necessary to finely adjust the filling thickness of each portion of the cavity of each model and conform the color tone of each portion to the periphery thereof.

The portion D3 was a high-Hue portion which could be appropriately restored using a curable paste corresponding to the A3 in the above-mentioned shade guide. The portion D2 was a medium-Hue portion which could be appropriately restored using a curable paste corresponding to the A2 in the shade guide. The portion D1 was a low-Hue portion which could be appropriately restored using a curable paste corresponding to the A1 in the shade guide.

In the class IV cavity 3 of FIG. 3, E was a portion which could be appropriately restored using a curable paste for enamel restoration.

In order to restore each of the above-mentioned portions of dentin, there were produced, by the following method, three kinds of curable pastes [a curable paste for restoration of high-Chroma portion (D3), a curable paste for restoration of medium-Chroma portion (D2), and a curable paste for restoration of low-Chroma portion (D1)].

First, a polymerizable base paste was produced. This polymerizable base paste was produced by compounding radically polymerizable monomers (bis-GMA: 10.80 mass parts, and 3G: 7.20 mass parts), photopolymerization initiators (CQ: 0.05 mass part, and DMBE: 0.10 mass part), a polymerization inhibitor (HQME: 0.03 mass part) and fillers (D-1: 32.8 mass parts, and D-2: 49.2 mass parts).

Then, the polymerizable base paste produced as above was colored by compounding therein the coloring agents of kinds and amounts shown in Table 1, to produce curable pastes. The color tone and contrast ratio of each curable paste are shown in Table 1.

Using each curable paste for dentin restoration, produced above, the class IV cavities 3 of the high-chromaticity model A and the low-chromaticity model B were restored. In the restoration, each curable paste was filled in a layer while adjusting, in each model, the filling thickness of each of the curable paste for restoration of high-Hue portion D3, the curable paste for restoration of medium-Hue portion D2 and the curable paste for low-Hue portion D1 so that the color tone of each restored portion conformed well to the periphery of cavity of model.

In each filling in the form of layer, the layer formed by filling was irradiated with a light using a light applicator for dental use and was photo-cured. Then, a next layer was formed by filling.

In this way, the restoration of dentin portion was finished. Then, a curable paste for enamel restoration was coated in the form of layer to form an enamel portion E as a surface layer, followed by photo-curing in the same manner as mentioned above. The coated thickness of the curable paste for enamel restoration was 1 mm in each of the high-chromaticity model A and the low-chromaticity model B. Incidentally, the cured body of the curable paste for enamel restoration showed a* of −3.27, b* of 5.18, L* of 50.68 and a contrast ratio of 0.48.

Figure 4:
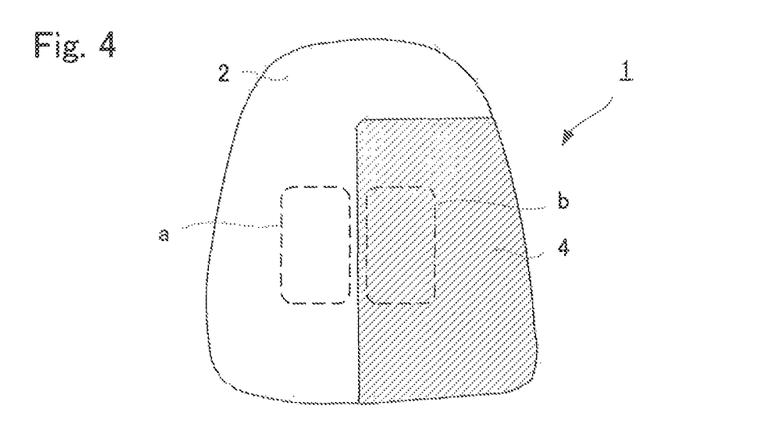
FIG. 4 is a front view indicating a state in which the class IV cavity formed in the model for tooth restoration, of FIG. 1 has been restored.

After the completion of the tooth restoration of the high-chromaticity model A and the low-chromaticity model B, the appearance (beauty) of the restored portion 4 of each model was evaluated visually. The evaluation was made by comparing the chromaticity and Value of the portion a surrounded by a dotted line, of the after-restoration model 1 for tooth restoration, of FIG. 4 with the chromaticity and Value of the portion b surrounded by a doted line, of the periphery of cavity and judging the conformability of the two chromaticities or two Values according to the following two-stage yardsticks.

Conformability of Chromaticity
O: The Hue and Chroma of the restored portion conform well to those of the periphery of the model and the difference between them is substantially unrecognizable visually.
X: The Hue and Chroma of the restored portion do not conform to those of the periphery of the model and the difference between them is recognizable visually.

Conformability of Value
O: The restored portion looks to be in harmony with the periphery of the model and the Value of the restored portion conforms well to that of the periphery.
X: The restored portion looks whitish (bright) or dull (dark) and the Value thereof does not conform to that of the periphery of the model.

The results are shown in Table 1. In the high-chromaticity model A and the low-chromaticity model B, the filling thicknesses of the curable paste for restoration of high-Chroma portion (D3), the curable paste for restoration of medium-Chroma portion (D2) and the curable paste for restoration of low-Chroma portion (D1) were different as mentioned above. However, since the Value L* of the cured body of each curable paste was in a fluctuation range of 3 or less (60.42−59.84=0.58), the prediction of the Value of the cured body of each curable paste was easy. As a result, in each of the high-chromaticity model A and the low-chromaticity model B, the chromaticity and Value of the restored portion conformed well to those of the periphery thereof.

Reference Example 1

In the same manner as in Example 1, there were produced curable pastes which gave cured bodies showing Values L* close to the upper limit (L*=75) specified by the present invention. The cured bodies showed a relatively large fluctuation (3.17) of L*; however, in each curable paste, the chromaticity and Value of the restored portion conformed well to those of the periphery thereof.

Example 2

In the same manner as in Example 1, there were produced curable pastes which gave cured bodies showing Values L* close to the lower limit (L*=55) specified by the present invention. In each cured body, the chromaticity and Value of the restored portion conformed well to those of the periphery thereof.

Example 3

In the same manner as in Example 1, there were produced curable pastes which gave cured bodies showing Values L* close to the upper limit (L*=75) specified by the present invention. The cured bodies showed a relatively large fluctuation (2.04) of L*; however, in each curable paste, the chromaticity and Value of the restored portion conformed well to those of the periphery thereof.

TABLE 1

| Kind of paste | | Pigment, mass part*1 | | | | Color tone of cured body | | | | Conformability of color tone | | | |
|---|---|---|---|---|---|---|---|---|---|---|---|---|---|
| | | White pigment | Yellow pigment | Red pigment | Blue pigment | L* | a* | b* | Contrast ratio | High-chromaticity model A | | Low-chromaticity model B | |
| | | | | | | | | | | Chromaticity | Value | Chromaticity | Value |
| Example 1 | D1 | 0.04000 | 0.00003 | 0.00015 | 0.00008 | 59.84 | −1.10 | 6.31 | 0.65 | ○ | ○ | ○ | ○ |
| | D2 | 0.04400 | 0.00040 | 0.00029 | 0.00013 | 60.12 | −1.03 | 8.49 | 0.87 | | | | |
| | D3 | 0.04700 | 0.00078 | 0.00038 | 0.00013 | 60.42 | 0.35 | 10.97 | 0.69 | | | | |
| Reference Example 1 | D1' | 0.09380 | 0.00030 | 0.00020 | 0.00010 | 73.20 | −1.46 | 6.89 | 0.73 | ○ | ○ | ○ | ○ |
| | D2' | 0.10050 | 0.00125 | 0.00045 | 0.00021 | 70.03 | −0.76 | 11.46 | 0.70 | | | | |
| | D3' | 0.10720 | 0.00150 | 0.00045 | 0.00020 | 71.53 | −1.29 | 13.11 | 0.71 | | | | |
| Example 2 | D1" | 0.02680 | 0.00010 | 0.00015 | 0.00010 | 56.36 | −1.16 | 4.17 | 0.59 | ○ | ○ | ○ | ○ |
| | D2" | 0.03015 | 0.00035 | 0.00029 | 0.00010 | 55.98 | −0.32 | 6.60 | 0.60 | | | | |
| | D3" | 0.03216 | 0.00082 | 0.00038 | 0.00005 | 56.15 | 0.16 | 10.66 | 0.61 | | | | |
| Example 3 | D1''' | 0.09179 | 0.00030 | 0.00023 | 0.00011 | 72.80 | −1.11 | 6.53 | 0.72 | ○ | ○ | ○ | ○ |
| | D2''' | 0.09715 | 0.00128 | 0.00045 | 0.00019 | 71.60 | −0.76 | 12.23 | 0.71 | | | | |
| | D3''' | 0.10519 | 0.00170 | 0.00050 | 0.00022 | 70.76 | −0.53 | 14.30 | 0.73 | | | | |

*1: Mass part relative to 100 mass parts of polymerizable base paste

Comparative Example 1

Restoration of tooth was conducted in the same manner as in Example 1 except that the curable paste for restoration of high-Chroma portion (D3), the curable paste for restoration of medium-Chroma portion (D2) and the curable paste for restoration of low-Chroma portion (D1), all used in restore of dentin were replaced by an A3 color paste, an A2 color paste and an A1 color paste, all of a commercial kit for dentin restoration (a commercial product A). The color chromaticity and contrast ratios of the cured bodies of the A3 color paste, the A2 color paste and the A1 color paste of the commercial product A are shown in Table 2.

The cured bodies of the pastes of the commercial product A showed a range of fluctuation of Value L*, of 7.88 (=59.05−51.17), which exceeded the fluctuation range specified by the present invention. Further, the cured body of the A3 paste showed Value of 51.17 which deviated the Value range of the present invention.

Comparative Example 2

Restoration of tooth was conducted in the same manner as in Comparative Example 1 except that the commercial kit used for dentin restoration was a commercial product B.

The cured bodies of the pastes of the commercial product B showed a range of fluctuation of Value L*, of 5.72 (=61.36−55.64), which exceeded the fluctuation range specified by the present invention.

In the restoration of the low-chromaticity model B, both chromaticity and Value conformed well to those of the periphery of the restored portion, as shown in Table 2.

Meanwhile, in the restoration of the high-chromaticity model A, chromaticity conformed well. However, Value did not conform in the thicknesses of the A3 color paste, the A2 color paste and the A1 color paste, in which the above-mentioned good Value could be achieved.

TABLE 2

| | | Color tone of cured body | | | | Conformability of color tone | | | |
|---|---|---|---|---|---|---|---|---|---|
| | | | | | | High-chromaticity model A | | Low-chromaticity model B | |
| | Kind | L* | a* | b* | Contrast ratio | Chromaticity | Value | Chromaticity | Value |
| Comparative Example 1 (commercial product A) | A1 | 59.05 | −1.32 | 2.92 | 0.60 | ○ | ○ | ○ | x |
| | A2 | 55.42 | −0.20 | 6.73 | 0.60 | | | | |
| | A3 | 51.17 | 0.80 | 10.01 | 0.61 | | | | |
| Comparative Example 2 (commercial product B) | A1 | 61.36 | −1.74 | 4.85 | 0.58 | ○ | x | ○ | ○ |
| | A2 | 56.13 | −1.31 | 6.76 | 0.57 | | | | |
| | A3 | 55.64 | −0.97 | 9.63 | 0.58 | | | | |

Also, the evaluation results of the appearance (beauty) of restored portion, in the high-chromaticity model A and the low-chromaticity model B are shown in Table 2. In the restoration of the high-chromaticity model A, both chromaticity and Value conformed well to those of the periphery of the restored portion, as shown in Table 2.

Meanwhile, in the restoration of the low-chromaticity model B, chromaticity conformed well to that of the periphery of the restored portion. However, Value did not conform to the periphery in the thickness ranges of the A3 color paste, the A2 color paste and the A1 color paste, in which the above-mentioned good Value could be achieved.

The invention claimed is:

1. A kit of materials for dentin restoration filled in a form of layers, the kit comprises a combination of a plurality of kinds of curable pastes each having a different color tone, wherein each curable paste exhibits Value L* of 55 to 75 and further wherein the plurality of kinds of curable pastes have a Value L* fluctuation range of 3 or less in the CIELab color system when cured bodies of 3.0 mm in thickness obtained by curing the curable pastes, are measured for color against a black background.

2. The kit of materials for dentin restoration filled in a form of layers according to claim 1, wherein each curable paste, when the cured body of 3.0 mm in thickness obtained by curing the curable paste is measured for color against a black background, exhibits a* of −5.0 to 3.0 and b* of 0 to 20 in the CIELab color system, at least either of a* and b* of the cured body differ from each other by 0.3 or more in the case of a* and by 1.0 or more in the case of b*, and each cured body has a different chromaticity.

3. The kit of materials for dentin restoration filled in a form of layers according to claim 1, wherein each curable paste exhibits a contrast ratio of 0.55 to 0.75 when the cured body of 1.0 mm in thickness by curing the curable paste is measured for the contrast ratio against a black background.

4. A kit of materials for tooth restoration, comprising the kit of materials for dentin restoration filled in a form of layers according to claim 1, and
  a kit of materials for enamel restoration, comprising of a plurality of kinds of curable pastes each having a different color tone when the cured body obtained by curing the curable paste is measured for color against a black background.

5. The kit of materials for tooth restoration according to claim 4, wherein each of the curable pastes constituting the kit of materials for enamel restoration exhibits Value L* of 45 to 65, a* of −5.0 to 3.0 and b* of −5 to 20, in the CIELab color system, when the cured body of 3.0 mm in thickness obtained by curing each curable paste is measured for color against a black background.

6. The kit of materials for tooth restoration according to claim 4, wherein each of the curable pastes constituting the kit of materials for enamel restoration exhibits a contrast ratio of 0.20 to 0.55 when the cured body of 1.0 mm in thickness obtained by curing each curable paste is measured for the contrast ratio.

7. A method for producing a kit of materials for dentin restoration filled in a form of layers according to claim 1, wherein the Value L* of each of the plurality of kinds of curable pastes is adjusted by changing the addition amount of a white coloring agent, while retaining the chromaticity a* and b* of each curable paste.

* * * * *